(12) United States Patent
Shinada et al.

(10) Patent No.: US 8,829,913 B2
(45) Date of Patent: Sep. 9, 2014

(54) DISCHARGE IONIZATION CURRENT DETECTOR

(75) Inventors: Kei Shinada, Uji (JP); Shigeyoshi Horiike, Uji (JP); Takahiro Nishimoto, Soraku-gun (JP); Katsuhisa Kitano, Ibaraki (JP)

(73) Assignees: Shimadzu Corporation, Kyoto-Shi (JP); Osaka University, Osaka (JP)

( * ) Notice: Subject to any disclaimer, the term of this patent is extended or adjusted under 35 U.S.C. 154(b) by 501 days.

(21) Appl. No.: 13/167,629

(22) Filed: Jun. 23, 2011

(65) Prior Publication Data

US 2011/0316551 A1 Dec. 29, 2011

(30) Foreign Application Priority Data

Jun. 28, 2010 (JP) .................................. 2010-146368

(51) Int. Cl.
    *G01N 27/62* (2006.01)
    *G01N 30/64* (2006.01)
    *G01N 27/70* (2006.01)

(52) U.S. Cl.
    CPC ............... *G01N 30/64* (2013.01); *G01N 27/70* (2013.01)
    USPC ........... 324/464; 324/465; 324/466; 324/467; 324/71.1; 250/251; 250/281; 73/28.02

(58) Field of Classification Search
    CPC ....... G01N 21/67; G01N 21/68; G01N 27/68; G01N 27/70; G01N 27/62; G01N 30/00; G01N 30/64
    USPC ............. 324/464; 250/287–288, 339.03, 374; 73/31.05
See application file for complete search history.

(56) References Cited

U.S. PATENT DOCUMENTS

| 5,394,092 A | | 2/1995 | Wentworth et al. ........... 324/464 |
| 5,594,346 A | * | 1/1997 | Stearns et al. ................ 324/464 |
| 5,892,364 A | * | 4/1999 | Monagle ....................... 324/464 |
| 2003/0006778 A1 | | 1/2003 | Aiki et al. |

FOREIGN PATENT DOCUMENTS

WO    WO 2009/119050 A1    10/2009

OTHER PUBLICATIONS

Kei Shinada et al, "Excited Ionization Current Detector for Gas Chromatography by Atmospheric Pressure Microplasma", Extended Abstracts of 55th Meeting of Japan Society of Applied Physics and Related Societies in 2008 Spring.
Kei Shinada et al., "Excited Ionization Current Detector for Gas Chromatography by Atmospheric Pressure Microplasma (II)", Extended Abstracts of 69th Meeting of Japan Society of Applied Physics and Related Societies in 2008 Autumn.

(Continued)

*Primary Examiner* — Arleen M Vazquez
*Assistant Examiner* — Son Le
(74) *Attorney, Agent, or Firm* — Bingham McCutchen LLP

(57) ABSTRACT

A technique for reducing an electromagnetic noise entering an electrode or a drift of a signal due to a fluctuation in the ambient temperature is provided to improve the S/N ratio of a signal originating from a component of interest. A dummy electrode having the same structure as an ion-collecting electrode is provided within a lower gas passage at a position where dilution gas with no sample gas mixed therein flows. A differential amplifier is provided to perform differential detection between output A of a current amplifier connected to the ion-collecting electrode and output B of a current amplifier connected to the dummy electrode. The differential signal is free from a common mode noise or drift and hence accurately reflects the amount of the component of interest.

6 Claims, 4 Drawing Sheets

(56) References Cited

OTHER PUBLICATIONS

Chinese Office Action mailed on Jun. 24, 2013 for the corresponding Chinese Patent App. No. 201110179411.8.

English translation of "Reason for Rejection" of Chinese Office Action dated Jun. 24, 2013 for Chinese Patent App. No. 201110179411.8.

* cited by examiner

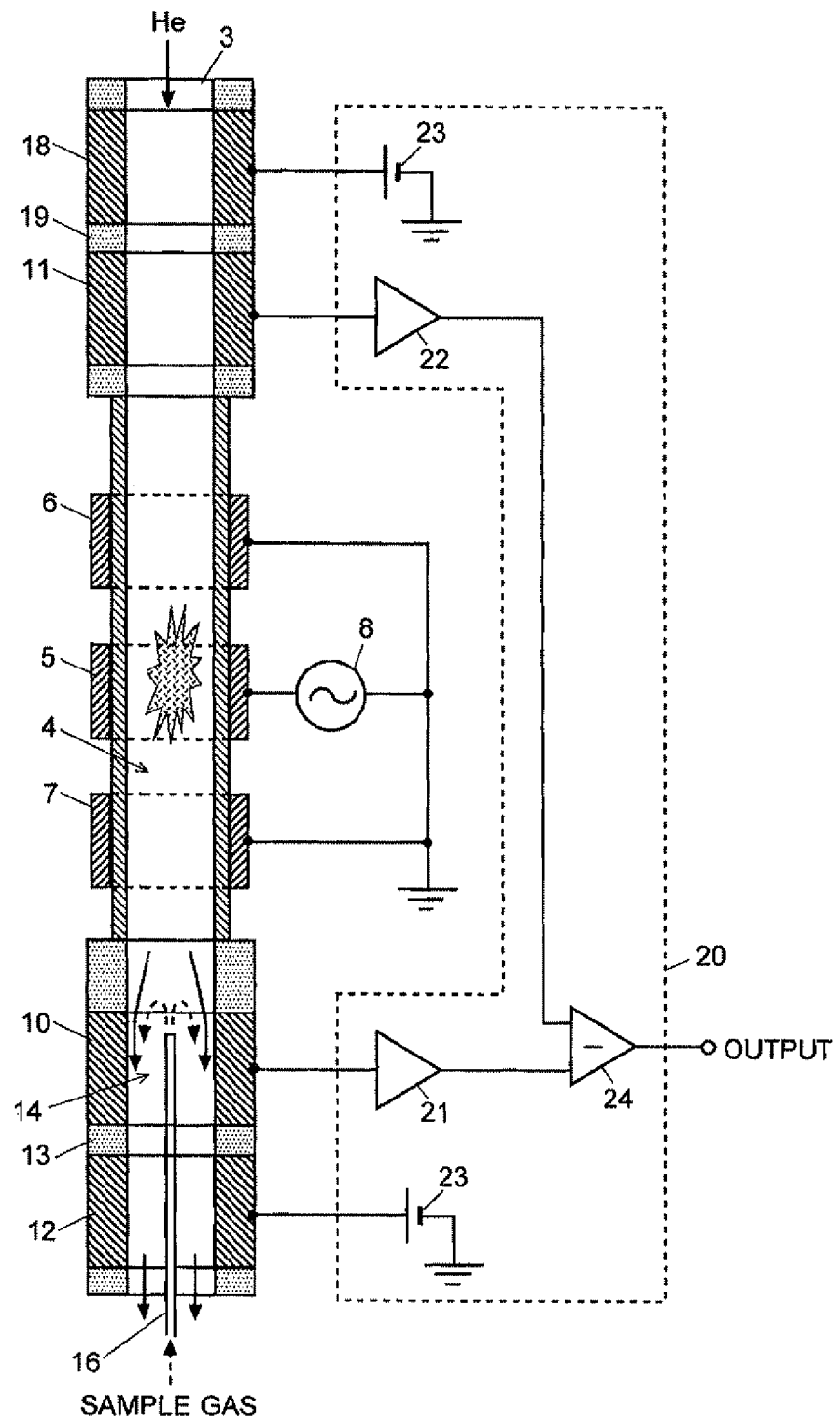

DISCHARGE IONIZATION CURRENT DETECTOR

TECHNICAL FIELD

The present invention relates to a discharge ionization current detector primarily suitable as a detector for a gas chromatograph (GC), and more specifically to a discharge ionization current detector using a low-frequency barrier discharge.

BACKGROUND ART

As a detector for a gas chromatograph, various types of detectors have been practically applied, such as a thermal conductivity detector (TCD), electron capture detector (ECD), flame ionization detector (FID), flame photometric detector (FPD), and flame thermionic detector (FTD). Among these detectors, the FID is most widely used, particularly for the purpose of detecting organic substances. The FID is a device that ionizes sample components in a sample gas by hydrogen flame and detects the resultant ion current. It can attain a wide dynamic range of approximately six orders of magnitude. However, the FID has the following drawbacks: (1) Its ionization efficiency is low, so that its minimum detectable amount is not sufficiently low; (2) Its ionization efficiency for alcohols, aromatic substances, and chlorine substances is low; (3) It requires hydrogen, which is a highly hazardous substance; therefore, an explosion-proof apparatus or similar kind of special equipment must be provided, which makes the entire system more difficult to operate. On the other hand, as a detector capable of high-sensitivity detection of various compounds from inorganic substances to low-boiling organic compounds, a pulsed discharge detector (PDD) has conventionally been known (for example, refer to Patent Document 1). In the PDD, the molecules of helium or another substance are excited by a high-voltage pulsed discharge. When those molecules return from their excited state to the ground state, they generate optical energy. This optical energy is utilized to ionize a molecule to be analyzed, and an ion current produced by the generated ions is detected to obtain a detection signal corresponding to the amount (concentration) of the molecule to be analyzed.

In most cases, the PDD can attain higher ionization efficiencies than the FID. For example, the ionization efficiency of the ND for propane is no higher than 0.0005%, whereas the PDD can achieve a level as high as 0.07%. Despite this advantage, the dynamic range of the PDD is not as wide as that of the FID; the fact is that the former is lower than the latter by one or more orders of magnitude. This is one of the reasons why the PDD is not as widely used as the FID.

The most probable constraining factors for the dynamic range of the conventional PDD are the unstableness of the plasma created for the ionization and the periodic fluctuation of the plasma state. To solve this problem, a discharge ionization current detector has been proposed (for example, refer to Patent Document 2). This detector uses a low-frequency AC-excited dielectric barrier discharge (which is hereinafter referred to as the "low-frequency barrier discharge") to create a stable and steady state of plasma. The plasma created by the low-frequency barrier discharge is non-equilibrium atmospheric pressure plasma, which does not become hot as easily as the plasma created by the radio-frequency discharge. Furthermore, the periodic fluctuation of the plasma, which occurs due to the transition of the voltage application state if the plasma is created by the pulsed high-voltage excitation, is prevented, so that a stable and steady state of plasma can be easily obtained. Based on these findings, the present inventors have conducted various kinds of research on the discharge ionization current detector using a low-frequency barrier discharge and have made many proposals on this technique (for example, refer to Patent Document 3 and Non-Patent Documents 1 and 2).

As just explained, the low-frequency barrier discharge can create a stable state of plasma and hence is generally advantageous for noise reduction. However, it is difficult to completely eliminate influences of electromagnetic noises that enter the ion-collecting electrode. It is also difficult to prevent the detection signal from a drift due to the fluctuation in the ambient temperature around the detection cell, which may be heated up to approximately 400 degrees Celsius for the detection of high-boiling components. In the case of a detector for GC or similar detector that is continuously operated for a considerable length of time during the measurement, the aforementioned noise or drift causes a fluctuation in the baseline of the detection signal and thereby decreases the S/N ratio of the signal originating from the components of interest.

BACKGROUND ART DOCUMENT

Patent Document

Patent Document 1: U.S. Pat. No. 5,394,092
Patent Document 2: U.S. Pat. No. 5,892,364
Patent Document 3: WO-A1 2009/119050

Non-Patent Document

Non-Patent Document 1: Shinada et al., "Taikiatsu Maikuro-purazuma Wo Mochiita Gasu Kuromatogurafu You Ion-ka Denryuu Kenshutsuki (Excited Ionization Current Detector for Gas Chromatography by Atmospheric Pressure Microplasma)", *Extended Abstracts of $55^{th}$ Meeting of Japan Society of Applied Physics and Related Societies in* 2008 *Spring*

Non-Patent Document 2: Shinada et al., "Taikiatsu Maikuro-purazuma Wo Mochiita Gasu Kuromatogurafu You Ion-ka Denryuu Kenshutsuki (II) (Excited Ionization Current Detector for Gas Chromatography by Atmospheric Pressure Microplasma: Part II)", *Extended Abstracts of $69^{th}$ Meeting of Japan Society of Applied Physics in* 2008 *Autumn*)

DISCLOSURE OF THE INVENTION

Problem to be Solved by the Invention

The present invention has been developed to solve the previously described problem, and a purpose thereof is to provide a discharge ionization current detector in which the influence of a noise due to an incoming electromagnetic noise or other factors and that of a drift due to a fluctuation in the ambient temperature or other factors are minimized so that the signal originating from a component of interest can be obtained with high sensitivity and accuracy

Means for Solving the Problems

The present invention aimed at solving the previously described problem is a discharge ionization current detector for ionizing and detecting a sample component in a sample gas where the sample gas is ionized using plasma created by discharge, including;

a) a plasma generation means for generating a dielectric barrier discharge by a low-frequency AC electric field within a gas passage in which a plasma gas flows, so as to create plasma from the plasma gas by the dielectric barrier discharge;

b) a sample-gas introduction passage for introducing a sample gas into the gas passage;

c) an ion-collecting electrode located within the gas passage, for detecting an ion current originating from a sample component in the sample gas ionized by an action of light emitted from the plasma created by the plasma generation means;

d) a dummy electrode located within the gas passage at such a position where the light emitted from the plasma reaches while neither the sample gas nor a component in the sample gas passes by; and e) a differential detection means for determining a differential signal between a detection signal obtained with the ion-collecting electrode and a detection signal obtained with the dummy electrode.

As the plasma gas, any type of gas selected from helium, argon, nitrogen, neon and xenon as well as any mixture thereof can be used.

The ion-collecting electrode and the dummy electrode should desirably be placed in the same surroundings and under the same conditions. Accordingly, it is preferable to expose both the ion-collecting electrode and the dummy electrode to the same kind of gas with the same flow rate. This can be achieved, for example, by a configuration in which the plasma gas that has passed by the ion-collecting electrode is made to directly pass by the dummy electrode, or a configuration in which a counterpart gas, which is of the same kind as the plasma gas and flows at the same flow rate against the plasma gas, is made to pass by the dummy electrode, and both the counterpart gas and the plasma gas are discharged from a point located between the dummy electrode and the ion-collecting electrode.

Effect of the Invention

In the discharge ionization current detector according to the present invention, for example, a common mode noise (e.g. an externally incoming electromagnetic noise) and a drift due to a fluctuation in the ambient temperature appear, with substantially similar forms, in both the detection signal obtained with the ion-collecting electrode and the detection signal obtained with the dummy electrode. Therefore, the influences of the common mode noise and the drift are barely noticeable in the differential signal obtained with the differential detection means. Thus, the noise superimposed on the baseline and the fluctuation in the baseline are reduced, so that the signal originating from that component can be detected with high accuracy and sensitivity even when the detection of a component of interest is continued for a considerable length of time.

BRIEF DESCRIPTION OF THE DRAWINGS

FIG. 5 is a schematic configuration diagram of a discharge ionization current detector according to still another embodiment of the present invention.

BEST MODE FOR CARRYING OUT THE INVENTION

Figure 1:
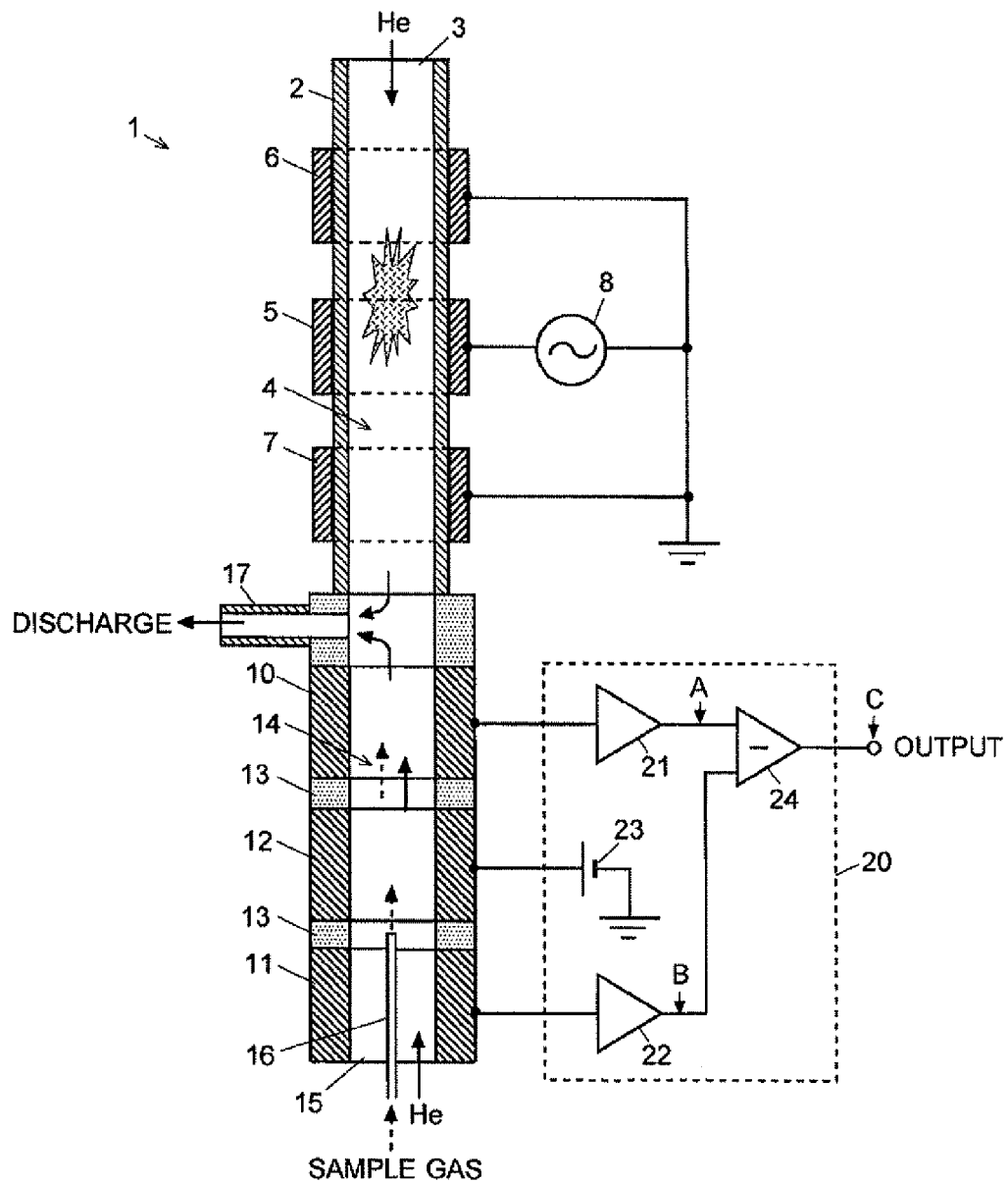
FIG. 1 is a schematic configuration diagram of a discharge ionization current detector according to one embodiment of the present invention.

A discharge ionization current detector according to one embodiment of the present invention is hereinafter described with reference to the attached drawings. FIG. 1 is a schematic configuration diagram of the discharge ionization current detector according to the present embodiment.

A discharge ionization current detector 1 of the present embodiment includes a cylindrical tube 2 made of a dielectric material, such as quartz. The upper portion of the inner space of this tube 2 is an upper gas passage 4, with its upper end serving as a plasma gas introduction port 3. One example of the cylindrical tube 2 is a quartz tube having an outer diameter of 3.9 mm. Ring-shaped plasma generation electrodes 5, 6, and 7, which are made of a metal (e.g. stainless steel or copper), are circumferentially provided at predetermined intervals on the outer wall surface of the cylindrical tube 2. According to this design, the dielectric wall of the cylindrical tube 2 between the upper gas passage 4 and the plasma generation electrodes 5, 6 and 7 functions as a dielectric coating layer that covers the electrodes 5, 6 and 7, and thereby enabling dielectric barrier discharge to occur.

Among the three plasma generation electrodes 5, 6 and 7, the central electrode 5 is connected to an excitation high-voltage power source 8, while the other electrodes 6 and 7 located on both sides of the central electrode 5 are connected to a ground. The structure in which the electrode 5, to which the high voltage is applied, is sandwiched between the grounded electrodes 6 and 7 prevents the plasma produced by the electric discharge from spreading toward the upstream and downstream ends of the gas stream, and thereby limiting the substantial plasma generation area to the space between the two plasma generation electrodes 6 and 7.

The excitation high-voltage power source 8 generates a low-frequency high AC voltage. Its frequency is within the range from 50 Hz to 100 kHz, and more preferably from 100 Hz to 20 kHz. The AC voltage may have any waveform, such as sine waves, rectangular waves, triangular waves or sawtooth waves.

An ion-collecting electrode 10, a bias voltage application electrode 12 and a dummy electrode 11 are arranged in the lower portion of the cylindrical tube 2 (on the downstream side of the gas), with insulators 13 made of alumina, PTFE resin or other materials disposed between them. These electrodes each consist of a cylindrical body having the same inner diameter. These cylindrical bodies internally define a lower gas passage 14 continuously extending from an upper gas passage 4 formed in the cylindrical tube 2. The lower end of the lower gas passage 14 is a dilution gas introduction port 15. A capillary tube 16 for introducing a sample gas into the lower gas passage 14 is inserted from the dilution gas introduction port 15 into the lower gas passage 14. The tip opening of the capillary tube 16 is located in a region surrounded by the bias voltage application electrode 12 or a region surrounded by the insulator 13 located between the bias voltage application electrode 12 and the dummy electrode 11.

A gas discharge tube 17 is connected to the upper portion of the lower gas passage 14, i.e. to the connection part between the upper portion of the lower gas passage 14 and the upper gas passage 4. This tube 17 is used for discharging plasma gas, dilution gas and sample gas from these gas passages 4 and 14.

The ion current detector 20 includes current amplifiers 21 and 22 with the same characteristics, a differential amplifier 24 for amplifying a differential signal of the two output signals respectively inputted from the current amplifiers 21 and 22, and a bias DC power source 23 for applying, to the bias voltage application electrode 12, a DC voltage of approximately several ten V to several hundred V. The inputs of the current amplifiers 21 and 22 are respectively connected to the ion-collecting electrode 10 and the dummy electrode 11.

A measurement operation of the discharge current ionization detector 1 of the present embodiment is hereinafter described.

As shown by the downward arrow in FIG. 1, helium gas as the plasma gas is supplied to the plasma gas introduction port 3 at a predetermined flow rate and flows downwards through the upper gas passage 4. Meanwhile, as shown by the upward arrows in FIG. 1, another stream of helium gas, which serves as the dilution gas, is supplied to the dilution gas introduction port 15 at a predetermined flow rate. (Basically, this flow rate is substantially equal to that of the plasma gas.) The dilution gas supplied into the lower gas passage 14 flows upwards. Additionally, a sample gas is supplied through the capillary tube 16. Within the lower gas passage 14, the dilution gas merges with the sample gas, forming a mixture of gas, and flows further upwards. The dilution gas, with the sample gas mixed therein, collides with the plasma gas in a region near the connection point of the gas discharge tube 17. Then, these gases are collectively discharged through the gas discharge tube 17. It should be noted that the plasma gas may be any kind of gas as long as it can be easily ionized. Examples include argon, nitrogen, neon and xenon in addition to helium as well as any mixture of two or more of these gases. The dilution gas should be the same kind of gas as the plasma gas.

When the plasma gas (helium) is flowing through the upper gas passage 4 in the previously described manner, the excitation high-voltage power source 8 is driven under the control of a controller (not shown) so as to apply a low-frequency high AC voltage between the plasma generation electrode 5 and each of the other electrodes 6 and 7. As a result, electric discharge occurs between the central electrode 5 and each of the other electrodes 6 and 7. This discharge is a dielectric barrier discharge since it occurs through the dielectric coating layer (the cylindrical tube 2). Due to this dielectric barrier discharge, the helium gas flowing through the upper gas passage 4 is ionized over a wide range, producing a cloud of plasma (i.e. atmospheric non-equilibrium micro-plasma).

The plasma created by the aforementioned discharge emits light, which passes through the upper gas passage 4 and the lower gas passage 14 to the region where the sample components exist. As a result, the molecules (or atoms) of the sample components in the sample gas are ionized primarily by photoionization. This ionization occurs within the lower gas passage 14 between the outlet end of the capillary tube 16 and a region near the connection point of the gas discharge tube 17. Due to the effect of the bias DC voltage of approximately 100 to 200 V applied from the bias DC power source 23 to the bias voltage application electrode 12, the sample ions generated by photoionization move to the ion-collecting electrode 10, giving electrons to or receiving electrons from this electrode 10. As a result, a signal corresponding to the amount of ions originating from the sample components appears at the output A of the current amplifier 21 connected to the ion-collecting electrode 10.

On the other hand, the ions originating from the sample components barely reach the dummy electrodes 11 since this electrode is located on the upstream side of the dilution gas relative to the point at which the sample gas exits from the capillary tube 16. Accordingly, no signal originating from the sample components noticeably appears at the output 13 of the current amplifier 22 connected to the dummy electrode 11.

Meanwhile, both the dummy electrode 11 and the ion-collecting electrode 10 are subjected to approximately the same level of externally incoming electromagnetic noises, the same level of noises due to the electrons or other components in the gas, or the same amount of drift associated with the fluctuation of the ambient temperature or other factors, because both electrodes 10 and 11 are in contact with the dilution-gas stream in approximately the same way, are almost equally affected by the DC electric field created by the bias voltage application electrode 12, and are placed under approximately the same ambient temperature.

Such a common mode noise or drift causes a noise or fluctuation to similarly appear in the baselines of both output signals A and B of the two current amplifiers 21 and 22. The differential amplifier 24 receives these two signals and removes the common mode noise and drift from both signals to produce an output signal C which primarily corresponds to the amount of ions originating from the sample components. Naturally, non-common mode noises (e.g. a random noise that occurs in each of the current amplifiers 21 and 22) cannot be removed by this method. However, removing the common mode noise and the drift considerably decreases the amount of noise or fluctuation in the baseline of the signal.

Figure 2:
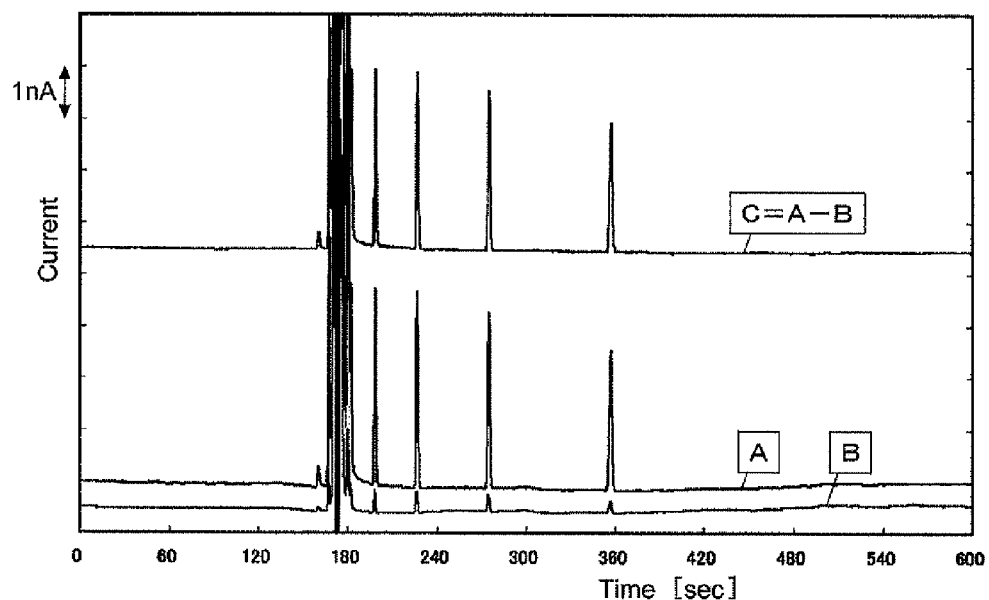
FIG. 2 is a graph showing an example of the detection signals actually measured with the discharge ionization current detector of the present embodiment.
Figure 3:
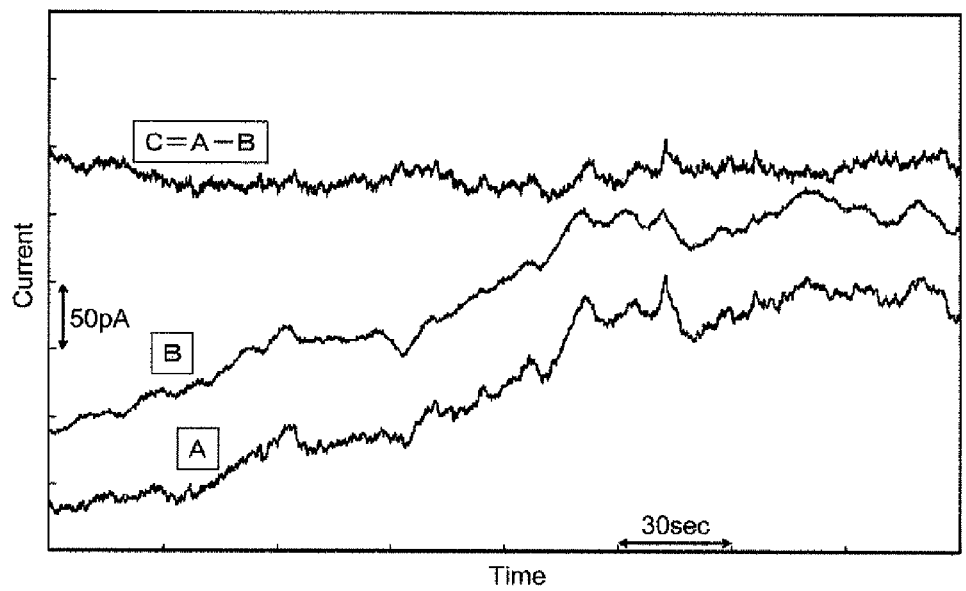
FIG. 3 is a partially enlarged view of the example shown in FIG. 2.

FIG. 2 is a graph showing an example of the detection signals actually measured with the discharge ionization current detector of the present embodiment, and FIG. 3 is a partially enlarged view of the example shown in FIG. 2. FIG. 3 demonstrates that the baseline fluctuation, which is likely to arise from a fluctuation in the ambient temperature, is significantly reduced in the output C of the differential amplifier 24. This is advantageous for achieving high S/N ratios and is particularly effective for improving the detection sensitivity (decreasing the lower detection limit) or widening the dynamic range.

Figure 4:
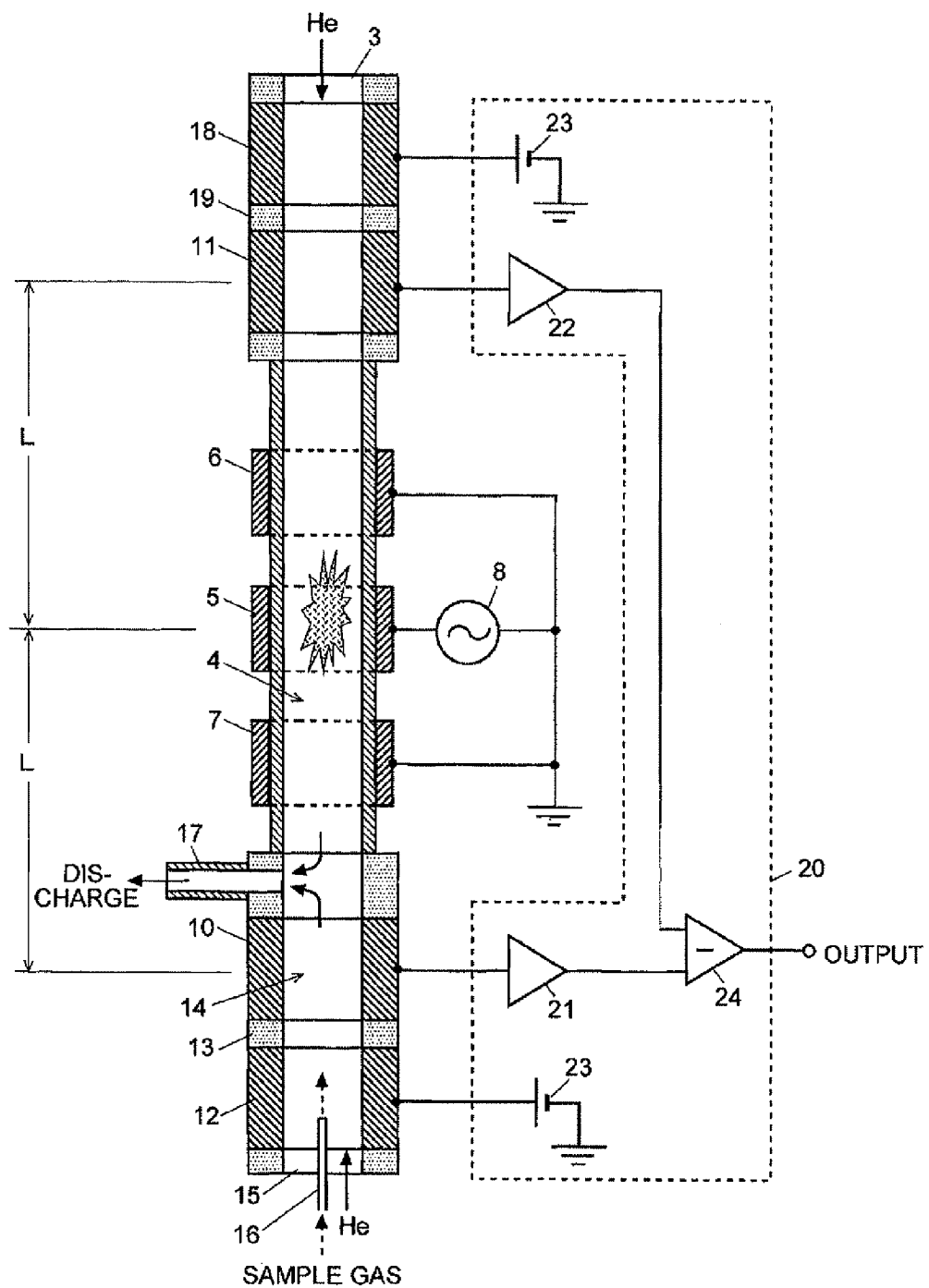
FIG. 4 is a schematic configuration diagram of a discharge ionization current detector according to another embodiment of the present invention.

Discharge ionization current detectors according to other embodiments of the present invention are hereinafter described by means of FIGS. 4 and 5. In FIGS. 4 and 5, the same components as shown in FIG. 1 are denoted by the same numerals. Unlike the previous embodiment (FIG. 1) in which both the ion-collecting electrode 10 and the dummy electrode 11 are placed in the lower gas passage 14, the device shown in FIG. 4 has the ion-collecting electrode 10 placed in the lower gas passage 14 and the dummy electrode 11 placed above the upper end of the upper gas passage 4. A bias voltage application electrode 18 is additionally provided for the dummy electrode 11, with an insulator 19 between them. The positional relationship between these electrodes 11 and 18 is made to be substantially identical to that between the ion-collecting electrode 10 and the bias voltage application electrode 12 so that the DC electric field acting on the dummy electrode 11 will be approximately equal to the DC electric field acting on the ion-collecting electrode 10. The distance from the plasma generation electrode 5 to the dummy electrode 11 is made to be approximately the same as the distance from the plasma generation electrode 5 to the ion-collecting electrode 10 so that the plasma light will make approximately equal effects on both the gas within the dummy electrode 11 (the plasma gas) and the gas within the ion-collecting electrode 10 (a mixture of the dilution gas and the sample gas).

According to the present configuration, plasma gas flows through the dummy electrode 11, while dilution gas flows through the ion-collecting electrode 10. When both gases are of the same kind (e.g. helium) and supplied at the same flow rate, the common mode noise or drift appearing on the output of the current amplifier 22 connected to the dummy electrode 11 will be substantially identical to those appearing on the output of the other current amplifier 21 connected to the ion-collecting electrode 10. An important difference of the present device from the previous embodiment is that none of the ions originating from the sample can reach the dummy electrode 11. Furthermore, since the effects of the plasma light on the dummy electrode 11 and the ion-collecting electrode 10 are equalized, the device performance in removing the common mode noise or drift is improved as compared to the previous embodiment.

The device shown in FIG. 5 is a variation of the previous one, in which no dilution gas is supplied upwards through the lower gas passage 14, while the downward flow of the plasma gas is made to pass through the lower gas passage 14, to be discharged from the lower end thereof after being mixed with the sample gas. This configuration is simpler, although the device performance in removing the noise or drift is slightly compromised since the ion-collecting electrode 10 and the dummy electrode 11 operate under different conditions: the plasma gas passing by the ion-collecting electrode 10 contains plasma-excited species, while the plasma gas passing by the dummy electrode 11 contains no such species.

It should be noted that the previously described embodiment is a mere example of the present invention. Any change, modification or addition appropriately made within the spirit of the present invention will naturally fall within the scope of claims of the present patent application.

Explanation of Numerals
1 . . . Discharge Ionization Current Detector
2 . . . Cylindrical Tube
3 . . . Plasma Gas Introduction Port
4 . . . Upper Gas Passage
5, 6, 7 . . . Plasma Generation Electrode
8 . . . Excitation High-Voltage Power Source
10 . . . Ion-Collecting Electrode
11 . . . Dummy Electrode
12, 18 . . . Bias Voltage Application Electrode
13, 19 . . . Insulator
14 . . . Lower Gas Passage
15 . . . Dilution Gas Introduction Port
16 . . . Capillary Tube
17 . . . Gas Discharge Tube
20 . . . Ion Current Detector
21, 22 . . . Current Amplifier
23 . . . Bias DC Power Source
24 . . . Differential Amplifier

The invention claimed is:

1. A discharge ionization current detector for ionizing and detecting a sample component in a sample gas where the sample gas is ionized using plasma created by discharge, comprising:
  a) a plasma generation means for generating a dielectric barrier discharge by a low-frequency AC electric field within a gas passage in which a plasma gas flows, so as to create plasma from the plasma gas by the dielectric barrier discharge;
  b) a sample-gas introduction passage for introducing a sample gas into the gas passage;
  c) an ion-collecting electrode located within the gas passage, for, detecting an ion current originating from a sample component in the sample gas ionized by an action of light emitted from the plasma created by the plasma generation means;
  d) a dummy electrode located within the gas passage at such a position where the light emitted from the plasma reaches while neither the sample gas nor a component in the sample gas passes by; and
  e) a differential detection means for determining a differential signal between a detection signal obtained with the ion-collecting electrode and a detection signal obtained with the dummy electrode.

2. The discharge ionization current detector according to claim 1, wherein the ion-collecting electrode and the dummy electrode are located opposite to each other across a region where plasma is created by the plasma generation means.

3. The discharge ionization current detector according to claim 2, wherein the plasma gas that has passed by the ion-collecting electrode is made to directly pass by the ion-collecting electrode.

4. The discharge ionization current detector according to claim 2, wherein a distance between the ion-collecting electrode and the aforementioned region is substantially equal to a distance between the dummy electrode and the aforementioned region.

5. A discharge ionization current detector for ionizing and detecting a sample component in a sample gas where the sample gas is ionized using plasma created by discharge, comprising:
  a) a plasma generation means for generating a dielectric barrier discharge by a low-frequency AC electric field within a gas passage in which a plasma gas flows, so as to create plasma from the plasma gas by the dielectric barrier discharge;
  b) a sample- gas introduction passage for introducing a sample gas into the gas passage;.
  c) an ion-collecting electrode located within the gas passage, for detecting an ion current originating from a sample component in the sample gas ionized by an action of light emitted from the plasma created by the plasma generation means;
  d) a dummy electrode located within the gas passage at such a position where the light emitted from the plasma reaches while neither the sample gas nor a component in the sample gas passes by; and
  e) a differential detection means for determining a differential signal between a detection signal obtained with the ion-collecting electrode and a detection signal obtained with the dummy electrode,
  wherein a counterpart gas, which is of a same kind as the plasma gas and flows at a same flow rate against the plasma gas, is made to pass by the dummy electrode, and both the counterpart gas and the plasma gas are discharged from a point located between the dummy electrode and the ion-collecting electrode.

6. A discharge ionization current detector for ionizing and detecting a sample component in a sample gas where the sample gas is ionized using plasma created by discharge, comprising:
  a) a plasma generation means for generating a dielectric barrier discharge by a low-frequency AC electric field within a gas passage in which a plasma gas flows, so as to create plasma from the plasma gas by the dielectric barrier discharge;
  b) a sample-gas introduction passage for introducing a sample gas into the gas passage;
  c) an ion-collecting electrode located within the gas passage, for detecting an ion current originating from a sample component in the sample gas ionized by an action of light emitted from the plasma created by the plasma generation means;

d) a dummy electrode located within the gas passage at such a position where the light emitted from the plasma reaches while neither the sample gas nor a component in the sample gas passes by; and
e) a differential detection means for determining a differential signal between a detection signal obtained with the ion-collecting electrode and a detection signal obtained with the dummy electrode, wherein the ion-collecting electrode and the dummy electrode are located opposite to each other across a region where plasma is created by the plasma generation means, and wherein a counterpart gas, which is of a same kind as the plasma gas and flows at a same flow rate against the plasma gas, is made to pass by the dummy electrode, and both the counterpart gas and the plasma gas are discharged from a point located between the dummy electrode and the ion-collecting electrode.

\* \* \* \* \*